US006458914B2

(12) United States Patent
Kimura et al.

(10) Patent No.: US 6,458,914 B2
(45) Date of Patent: Oct. 1, 2002

(54) METHOD FOR MANUFACTURING DIALKYL CARBONATE

(75) Inventors: Takato Kimura; Tomoaki Shimoda; Masahide Tanaka, all of Ichihara (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/882,339

(22) Filed: Jun. 14, 2001

(30) Foreign Application Priority Data

| Jun. 28, 2000 | (JP) | ................................. 2000-195029 |
| Jun. 28, 2000 | (JP) | ................................. 2000-195030 |
| Jun. 28, 2000 | (JP) | ................................. 2000-195031 |
| Jun. 28, 2000 | (JP) | ................................. 2000-195032 |

(51) Int. Cl.[7] ............................................... C08G 64/00
(52) U.S. Cl. ......................................... 528/196; 528/198
(58) Field of Search ................................. 528/196, 198

(56) References Cited

U.S. PATENT DOCUMENTS

| 4,218,391 A | 8/1980 | Romano et al. ............. 260/463 |
| 4,361,519 A | 11/1982 | Hallgren |
| 4,785,130 A | 11/1988 | Bhattacharya ............... 558/277 |
| 5,258,541 A | 11/1993 | Yokota et al. |

FOREIGN PATENT DOCUMENTS

| EP | 534 545 B1 | 3/1993 |
| JP | 5-4024827 | 2/1979 |
| JP | 2-251524 | 9/1990 |
| JP | 9194430 | 7/1997 |

*Primary Examiner*—Terressa M. Boykin

(57) ABSTRACT

The specification describes a method for manufacturing dialkyl carbonate by reacting carbon monoxide, oxygen and alcohol in the presence of a catalyst. The catalyst is produced by reacting together ingredients including a cupric halide and an alkoxide compound of a group III through VII metal.

16 Claims, No Drawings

METHOD FOR MANUFACTURING DIALKYL CARBONATE

The present application is a U.S. non-provisional application based upon and claiming priority from Japanese Application Nos. 2000-195029, 2000-195030, 2000-195031, and 2000-195032, with a filing date of Jun. 28, 2000 which are hereby incorporated by reference.

FIELD OF THE INVENTION

The present invention concerns a method for manufacturing dialkyl carbonate. More specifically, it concerns a method for efficiently manufacturing dialkyl carbonate from CO, $O_2$, and alcohol.

BACKGROUND OF THE INVENTION

In recent years, aromatic polycarbonates have come to be widely used in numerous fields as engineering plastics showing outstanding mechanical properties such as impact resistance, as well as outstanding heat resistance, transparency, etc.

The so-called phosgene method, in which aromatic dihydroxide compounds such as bisphenol are reacted with phosgene by the interfacial polycondensation method, has been widely used as a method for manufacturing these aromatic polycarbonates. However, the phosgene method currently in industrial use has been reported to show many drawbacks, such as the fact that highly toxic phosgene must be used, the fact that there are problems with processing the large amounts of sodium hydroxide produced as a byproduct, and health and pollution problems resulting from the methylene chloride ordinarily used as a reaction solvent.

The process of transesterification (melting method) of aromatic dihydroxy compounds and carbonic acid diesters using alkali metal compounds such as sodium hydroxide as catalysts is known as a method for manufacturing aromatic polycarbonates other than the phosgene method. This method has attracted widespread attention due to its advantage of allowing manufacturing using inexpensive aromatic polycarbonates and the fact that it is desirable from an environmental hygiene standpoint as it does not require the use of toxic compounds such as phosgene and methylene chloride.

In manufacturing polycarbonate using such melt methods, diaryl carbonates such as diphenyl carbonate are used as carbonic acid diesters. This diaryl carbonate, as disclosed in Japanese Unexamined Patent Application Publication No. H9-194430, is manufactured by transesterification of dialkyl carbonate and a hydroxyl-group-containing aromatic hydrocarbon such as phenol. The dialkyl carbonate used as a raw material for this diaryl carbonate is manufactured from carbon monoxide, oxygen, and alcohol using a catalyst composed of a cuprous halide such as cuprous chloride.

For example, when methanol is used as an alcohol, dimethyl carbonate is manufactured by the following reaction:

$$2\ CH_3OH + CO + 1/2 O_2 \rightarrow (CH_3O)_2CO + H_2O$$

Concerning the cuprous chloride used as a catalyst in this case, in a primary reaction, cupric methoxychloride is formed by the reaction:

$$2CuCl + 2CH_3OH + 1/2 O_2 \rightarrow 2Cu(OCH_3)Cl + H_2O$$

and it is thought that regeneration occurs in the following secondary reaction:

$$2Cu(OCH_3)Cl + CO \rightarrow (CH_3O)_2CO + 2CuCl.$$

Moreover, the method of adding a hydroacid halide to the reaction system in order to increase the catalytic activity of the cuprous halide used as the catalyst has been presented (cf. Japanese Unexamined Patent Application No. H5-194327).

However, in the above method in which a cuprous halide is used as a catalyst, as the conversion rate of the aforementioned cupric alkoxy chloride formed is low, the yield of the dialkyl carbonate obtained may not be sufficient, and the catalyst used may cause clogging of the reaction vessel and tubing, impairing manufacturing efficiency.

SUMMARY OF THE INVENTION

Against this backdrop, the inventors of the present invention conducted thorough studies on methods for efficiently manufacturing dialkyl carbonate, and they discovered that by using a combination of specified copper compounds and other metal compounds as a catalyst, it is possible to produce dialkyl carbonate in a high yield while maintaining high catalytic activity during the reaction without clogging of the reaction vessel, tubing, etc., by the catalyst, thus perfecting the present invention.

The present invention was developed based on the above prior art in order to provide a method for efficiently manufacturing dialkyl carbonate from CO, $O_2$, and alcohol.

The method for manufacturing dialkyl carbonate of the present invention uses one of catalysts 1–5 below as a catalyst in the manufacture of dialkyl carbonate using carbon monoxide, oxygen, and alcohol as starting materials.

Catalyst 1: A catalyst prepared by mixing (i) a cupric halide and (ii-1) an alkoxide compound of a metal from groups III through VIII of the periodic table.

Catalyst 2: A catalyst prepared by mixing (i) a cupric halide, (ii-2) a metal halide compound from groups III through VIII of the periodic table, (ii-3) at least one compound selected from the group composed of an alkali metal alkoxide, an alkaline earth metal alkoxide, a quaternary ammonium alkoxide having Formula (1) below, and a quaternary phosphonium alkoxide having Formula (2) below, with it being possible to use a substance containing the following:

$$R^1R^2R^3R^4NOR^5 \tag{1}$$

$$R^1R^2R^3R^4POR^5 \tag{2}$$

(where $R^1$–$R^4$ may be the same or different and denote hydrogen atoms or hydrocarbon groups having 1–20 carbon atoms, and $R^5$ denotes a hydrocarbon group having 1–20 carbon atoms.)

Catalyst 3: A catalyst prepared by mixing (I) a copper halide and (II) an alkaline earth metal halide.

Catalyst 4: A catalyst prepared by mixing (a) a copper compound not containing halogen atoms and (b) a halide acid.

Catalyst 5: A catalyst prepared by mixing (A) a copper compound not containing halogen atoms and (B) an alkoxide compound capable of being reacted with the aforementioned (A) copper compound to produce a copper alkoxide.

The alcohol used in the manufacturing method for dialkyl carbonate of the present invention should preferably be methanol.

DETAILED DESCRIPTION OF THE INVENTION

The following is a detailed description of the method for manufacturing dialkyl carbonate of the present invention.

We will first explain the starting materials and catalysts used in the method for manufacturing dialkyl carbonate of the present invention.

STARTING MATERIALS AND CATALYSTS

In the present invention, carbon monoxide (CO), oxygen (O$_2$), and alcohol are used as starting materials.

There are no particular restrictions on the alcohol used as a starting material, with examples including methanol, ethanol, propanol, butanol, isopropanol, isobutanol, and hexanol. Among these, methanol should preferably be used.

Catalysts 1–5 below may be used as the catalyst of the present invention.

Catalyst 1: A catalyst composed of (i) a cupric halide and (ii) an alkoxide compound of a metal from groups III through VIII of the periodic table.

Catalyst 2: A catalyst composed of (i) a cupric halide, (ii-2) a metal halide compound from groups III through VIII of the periodic table, (ii-3) at least one compound selected from the group composed of an alkali metal alkoxide, an alkaline earth metal alkoxide, a quaternary ammonium alkoxide having Formula (1) below, and a quaternary phosphonium alkoxide having Formula (2) below, with it being possible to use a substance containing the following:

  (1)

  (2)

(where $R^1$–$R^4$ may be the same or different and denote hydrogen atoms or hydrocarbon groups having 1–20 carbon atoms, and $R^5$ denotes a hydrocarbon group having 1–20 carbon atoms.)

Catalyst 3: A catalyst composed of (I) a copper halide and (II) an alkaline earth metal halide.

Catalyst 4: A catalyst composed of (a) a copper compound not containing halogen atoms and (b) a halide acid.

Catalyst 5: A catalyst composed of (A) a copper compound not containing halogen atoms and (B) an alkoxide compound capable of being reacted with the aforementioned (A) copper compound to produce a copper alkoxide.

The various catalysts are explained below.

Catalysts 1 and 2

Examples of (i) the cupric halide used in catalyst 1 include cupric chloride, cupric fluoride, cupric bromide, and cupric iodide. These may also be used in mixtures of two or more. Among these substances, cupric chloride is preferred.

An example of (ii-1) the alkoxide compound of a metal from groups III through VIII of the periodic table is the alkoxide compound shown in Formula (3) below.

  (3)

(In Formula 1 [sic], M denotes a metal from groups III through VIII of the periodic table, $R^a$ denotes a hydrocarbon group having 1–20 carbon atoms, and n denotes the valence of M.)

Examples of the metal from groups III through VIII of the periodic table include metals such as aluminum, gallium, indium, yttrium, thallium, silicon, germanium, titanium, tin, zirconium, lead, hafnium, vanadium, antimony, niobium, tantalum, chromium, tellurium, molybdenum, tungsten, iron, cobalt, nickel, ruthenium, rhodium, palladium, and platinum. Examples of the hydrocarbon group having 1–20 carbon atoms include alicyclic hydrocarbon groups and aromatic hydrocarbon groups such as phenyl, tolyl, and naphthyl groups, which may optionally contain linear alkyl groups such as methyl, ethyl, propyl, butyl, pentyl, hexyl, and octyl groups, branched alkyl groups such isopropyl and isobutyl groups, and branched groups such as cyclopentyl, cyclohexyl, and methylcyclohexyl groups.

These metal alkoxides from groups III through VIII of the periodic table may be mixed in combinations of two or more. Among these, metal alkoxides such as aluminum triethoxide, titanium tetramethoxide, aluminum trimethoxide, iron trimethoxide, cobalt dimethoxide, nickel dimethoxide, vanadium tetramethoxide, and tin tetramethoxide are preferred.

In catalyst 2, instead of (ii-1) the metal alkoxide from groups III through VIII of the periodic table, (ii-2) a metal halide from groups III through VIII of the periodic table and (ii-3) at least one compound selected from the group composed of an alkali metal alkoxide or alkaline earth metal alkoxide of Formula (4) [sic] below, a quaternary ammonium alkoxide of Formula 1 below, or a quaternary phosphonium alkoxide of Formula (2) below may be used.

  (3)

  (1)

  (2)

(In the formula, A denotes an alkali metal or alkaline earth metal, $R^b$ denotes a hydrocarbon group having 1–20 carbon atoms, and m denotes the valence of A. Furthermore, $R^1$–$R^4$ may be the same or different and are hydrogen atoms or hydrocarbon groups having 1–20 carbon atoms, and examples of hydrocarbon groups having 1–20 carbon atoms are substances identical to those shown in the above examples.)

Preferred examples of the halide of a metal from groups III through VIII of the periodic table include fluorides, chlorides, bromides, and iodides of aluminum, gallium, indium, yttrium, thallium, silicon, germanium, titanium, tin, zirconium, lead, hafnium, vanadium, antimony, niobium, tantalum, chromium, tellurium, molybdenum, tungsten, iron, cobalt, nickel, ruthenium, rhodium, palladium, and platinum, with chlorides being preferred and substances such as aluminum chloride and titanium tetrachloride being particularly preferred.

These halides may be used either individually or in combinations of two or more.

Specific examples of alkali metal alkoxides include sodium methoxide, lithium methoxide, potassium methoxide, rubidium methoxide, cesium methoxide, sodium ethoxide, lithium ethoxide, potassium ethoxide, rubidium ethoxide, cesium ethoxide, sodium propoxide, lithium propoxide, potassium propoxide, rubidium propoxide, cesium propoxide, sodium butoxide, lithium butoxide, potassium butoxide, rubidium butoxide, cesium butoxide, sodium pentoxide, lithium pentoxide, potassium pentoxide, rubidium pentoxide, cesium pentoxide, sodium hexoxide, lithium hexoxide, potassium hexoxide, rubidium hexoxide, cesium hexoxide, sodium heptoxide, lithium heptoxide, potassium heptoxide, rubidium heptoxide, cesium heptoxide, sodium octoxide, lithium octoxide, potassium octoxide, rubidium octoxide, cesium octoxide, sodium phenoxide, lithium phenoxide, potassium phenoxide, rubidium phenoxide, and cesium phenoxide.

Specific examples of alkaline earth metal alkoxides include mono- and dialkoxide compounds such as methoxides, ethoxides, propoxides, butoxides, pentoxides, hexoxides, heptoxides, octoxides, and phenoxides of beryllium, magnesium, calcium, strontium, and barium.

Specific examples of quaternary ammonium alkoxides include alkoxide compounds such as tetramethyl ammonium, tetraethyl ammonium, tetrapropyl ammonium, tetrabutyl ammonium, tetrapentyl ammonium, and tetraheptyl ammonium methoxides and tetraoctyl ammonium and tetraphenyl ammonium methoxides, ethoxides, propoxides, butoxides, pentoxides, hectoxides, heptoxides, octoxides, and phenoxides.

Specific examples of quaternary phosphonium alkoxides include alkoxide compounds such as tetramethyl phosphonium, tetraethyl phosphonium, tetrapropyl phosphonium, tetrabutyl phosphonium, tetrapentyl phosphonium, and tetraheptyl phosphonium methoxides and tetraoctyl phosphonium and tetraphenyl phosphonium methoxides, ethoxides, propoxides, butoxides, pentoxides, hectoxides, heptoxides, octoxides, and phenoxides.

These alkoxide compounds may be used individually or in combinations of two or more.

The aforementioned (ii-2) halide of a metal from groups III through VIII of the periodic table and (ii-3) at least one compound selected from the group composed of alkali metal alkoxides, alkaline earth metal alkoxides, quaternary ammonium alkoxides, and quaternary phosphonium alkoxides are reacted as follows to produce an alkoxide compound of a metal from groups III through VIII of the periodic table.

① In the case of an alkali metal, quaternary ammonium, or quaternary phosphonium alkoxide:

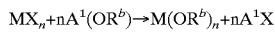

$$MX_n + nA^1(OR^b) \rightarrow M(OR^b)_n + nA^1X$$

② In the case of an alkaline earth metal alkoxide:

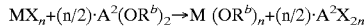

$$MX_n + (n/2) \cdot A^2(OR^b)_2 \rightarrow M(OR^b)_n + (n/2) \cdot A^2 X_{2n}$$

(In the above reaction formulas, X denotes a halogen, M denotes a metal from groups III through VIII of the periodic table, and n denotes the valence of M. Moreover, $A^1$ denotes an alkali metal, quaternary ammonium, or quaternary phosphonium, $A^2$ denotes an alkaline earth metal, and $R^b$ denotes a hydrocarbon group having 1–20 carbon atoms.)

In the present invention, an alkoxide compound of a metal from groups III through VIII of the periodic table obtained in the above reactions may be used as catalyst 2; alternatively, (ii-2) a metal halide from groups III through VIII of the periodic table that is either unreacted or in the process of being reacted and (ii-3) at least one compound selected from the group composed of an alkali metal alkoxide or alkaline earth metal alkoxide having Formula (2) above, a quaternary ammonium alkoxide having Formula (3) above, and a quaternary phosphonium alkoxide having Formula (4) [sic] above may also be used as catalyst 2.

The ratio of (ii-2) the metal halide from groups III through VIII of the periodic table to (ii-3) the alkoxide compound selected from the group composed of an alkali metal alkoxide, an alkaline earth metal alkoxide, a quaternary ammonium alkoxide, and a quaternary phosphonium alkoxide (alkoxy groups in alkoxide compound/halogens in halide) should be a molar ratio in the range of 0.5–2.0, and preferably 0.9–1.5.

In reacting the aforementioned alkoxide compound and the aforementioned halide, the reaction should preferably be carried out at a temperature of 0–120° C. using $R^bOH$ as a solvent. The reaction mixture composed of the alkoxide compound of a metal from groups III through VIII of the periodic table obtained and the alkali metal, alkaline earth metal, quaternary ammonium, or quaternary phosphonium halide may be used as is, but the alkali metal, alkaline earth metal, quaternary ammonium, or quaternary ammonium halide $(AX_m)$ produced may also be removed by a process such as filtration.

Catalyst 3

Examples of (I) the copper halide used as catalyst 3 include cuprous chloride, cupric chloride, cuprous fluoride, cupric fluoride, cuprous bromide, cupric bromide, cuprous iodide, and cupric iodide. Of these substances, a monovalent copper compound is preferred, with cuprous chloride being particularly well-suited from the standpoint of activity.

Examples of (II) the alkali metal halide include magnesium chloride, magnesium fluoride, magnesium bromide, magnesium iodide, calcium chloride, calcium fluoride, calcium bromide, calcium iodide, strontium chloride, strontium fluoride, strontium bromide, strontium iodide, barium chloride, barium fluoride, barium bromide, and barium iodide.

These copper halides and alkali metal halide compounds may be used either individually or in mixtures of two or more. Among these, magnesium chloride and barium chloride are particularly preferred from the standpoint of activity.

Catalyst 4

Examples of the (a) copper compound not containing halogen atoms used as catalyst 4 include the copper alkoxide compounds of Formulas (4) and (5) below.

$$Cu(OR)_2 \qquad (4)$$

$$Cu(OR) \qquad (5)$$

In the formula, R denotes a hydrocarbon group having 1–20 carbon atoms. Examples of hydrocarbon groups having 1–20 carbon atoms that may be used include alicyclic hydrocarbon groups that may have linear alkyl groups such as methyl, ethyl, propyl, butyl, pentyl, hexyl, and octyl groups, branched alkyl groups such as isopropyl and isobutyl groups, or branched groups such as cyclopentyl, cyclohexyl, or methylcyclohexyl groups and aromatic hydrocarbon groups such as phenyl, tolyl, and naphthyl groups. Examples of these copper alkoxide compounds that may be used include copper dimethoxide, copper diethoxide, copper dipropoxide, copper dibutoxide, copper diphenoxide, copper methoxide, copper ethoxide, copper propoxide, copper butoxide, and copper phenoxide. Moreover, copper chelate compounds such as copper acetylacetonate chelate may also be used.

Furthermore, examples of copper compounds not containing halogen atoms that may be used include inorganic copper compounds such as cupric hydroxide $(Cu(OH)_2)$, cupric nitrate $(Cu(NO_3)_2)$, cupric acetate $(Cu(OCOCH_3)_2)$, cupric oxalate, cupric phosphate, cupric phthalate, cupric formate, cupric sulfate $(CuSO_4)$, basic cupric carbonate $(CuCO_3 \cdot Cu(OH) \cdot H_2O)$, cuprous hydroxide (CuOH), cuprous nitrate $(CuNO_3)$, cuprous acetate $(CuOCOCH_3)$, cuprous oxalate, cuprous phosphate, cuprous phthalate, cuprous formate, and cuprous sulfate $(Cu_2SO_4)$.

Among these substances, divalent copper-containing compounds are preferred, preferably at least one compound selected from the group composed of copper dimethoxide, copper diethoxide, copper dipropoxide, cupric hydroxide $(Cu(OH)_2)$, cupric nitrate $(Cu(NO_3)_2)$, cupric acetate $(Cu(OCOCH_3)_2)$, cupric sulfate $(CuSO_4)$, and basic copper carbonate $(CuCO_3 \cdot Cu(OH) \cdot H_2O)$.

Two or more of these copper compounds not containing halogen atoms may also be used in combination.

Examples of (b) halide acids include hydrogen halide (HX: X denotes a halogen) acids such as hydrofluoric acid (HF), hydrochloric acid (HCl), and bromic acid (HBr) Two or more halide acids may also be used in combination.

Among these substances, hydrochloric acid is preferred in the present invention from the standpoint of activity.

Catalyst 5

An example of (A) the copper compound not containing halogen atoms used in catalyst 5 is the same compound used in the aforementioned catalyst 4.

These copper compounds not containing halogen atoms may also be used in combinations of two or more.

Moreover, as (B) the alkoxide compound that is reacted with the aforementioned (A) copper compound to produce a copper alkoxide, one should preferably use at least one compound selected from the group composed of an alkali metal alkoxide, an alkaline earth metal alkoxide, the quaternary ammonium alkoxide of Formula (1) above, and the quaternary phosphonium alkoxide of Formula (2) above.

Examples of the alkali metal alkoxide include an alkaline earth metal alkoxide, a quaternary ammonium alkoxide, and a quaternary phosphonium, the same as the substances mentioned above. These alkoxide compounds may also be used in combinations of two or more.

The aforementioned (A) copper compound not containing halogen atoms and (B) the alkoxide compound capable of being reacted with (A) the aforementioned copper compound to produce a copper alkoxide are reacted to produce a copper alkoxide not containing halogen atoms.

When the aforementioned catalysts 1–5 are used, catalytic activity in manufacturing of dialkyl carbonate using carbon monoxide, oxygen, and alcohol as starting materials is high and the reaction is stable, making it possible to maintain catalytic activity over long periods.

MANUFACTURING OF DIALKYL CARBONATE

In the present invention, the aforementioned catalysts 1–5 are used in manufacturing dialkyl carbonate using carbon monoxide, oxygen, and alcohol as starting materials.

When catalyst 1 or 2 is used, one first takes (i) a cupric halide and (ii-1) an alkoxide compound of a metal from groups III through VIII of the periodic table, or (i) a cupric halide, (ii-2) a metal halide from groups III through VIII of the periodic table, and (ii-3) at least one compound selected from the group composed of an alkali metal alkoxide, an alkaline earth metal alkoxide, the quaternary ammonium alkoxide of Formula (1) above, and the quaternary phosphonium alkoxide of Formula (2) above, adds them to the alcohol used as a raw material, and carries out a reaction to prepare raw material alcohol containing catalytic components.

The (i) cupric halide, (ii-1) metal alkoxide from groups III through VIII of the periodic table, and cupric halide should be added in the amount of 0.001–1.0 mol, and preferably 0.005–0.2 mol per mol of alcohol.

The (ii-1) alkoxide compound of a metal from groups III through VIII of the periodic table should be added in the amount of 0.05–2.0 mol, and preferably 0.1–1.2 mol with respect to (i) the cupric halide.

In the case of use of catalyst 2, when (ii-2) the metal halide from groups III through VIII of the periodic table and (ii-3) the alkoxide compound selected from the group composed of the aforementioned alkali metal alkoxide, alkaline earth metal alkoxide, quaternary ammonium alkoxide, and quaternary phosphonium alkoxide are used as the catalyst, (ii-2) the metal halide from groups III through VIII of the periodic table should be added in the amount of 0.05–2.0 mol, and preferably 0.1–1 mol with respect to (i) the cupric halide. Moreover, the (ii-3) alkoxide compound, with respect to (ii-2) the metal halide from groups III through VIII of the periodic table, should be added in a molar ratio (alkoxy groups in (ii-3) the alkoxide compound/halogens in (ii-2) the halogen compound) of 0.5–2.0, and preferably 0.9–1.5.

When catalyst 3 is used, specifically, one first adds the catalyst composed of (I) the copper halide and (II) the alkali metal halide to the raw material alcohol and then reacts it to prepare raw material alcohol containing catalytic components.

(I) The copper halide should be added in the amount of 0.001–1.0 mol, and preferably 0.005–0.2 mol per mol of alcohol.

The catalyst composed of (II) an alkali metal halide should be added with respect to (I) the copper halide in an alkaline earth metal/copper atom ratio of 0.05–2.0 mol, and preferably 0.1–1.2 mol.

When catalyst 4 is used, specifically, one first adds the catalyst composed of (a) the copper compound not containing halogen atoms and (b) a halide acid to the raw material alcohol and reacts the mixture in order to obtain raw material alcohol containing catalytic components.

Moreover, the (a) copper compound not containing halogen atoms should be added in the amount of 0.001–1.0 mol, and preferably 0.005–2.0 mol per mol of alcohol.

The catalyst composed of (b) a halide acid should be added with respect to (a) the copper compound not containing halogen atoms with a ratio of Cl atoms in the halide acid to the copper atoms in the copper compound (Cl/Cu) of 0.05–2.0 mol, and preferably 0.1–1.2 mol.

When catalyst 5 is used, one first adds the catalyst composed of (A) a copper compound not containing halogen atoms and (B) an alkoxide compound capable of producing copper alkoxide when reacted with (B) the aforementioned (A) copper compound to the raw material alcohol and then carries out the reaction in order to prepare raw-material alcohol containing catalytic components.

Furthermore, (A) the copper compound not containing halogen atoms should be added in the amount of 0.001–1.0 mol, and preferably 0.005–2.0 mol per mol of alcohol.

The aforementioned (A) copper compound and (B) alkoxide compound capable of being reacted with said copper compound to produce a copper alkoxide should be added in such a way that the molar ratio of the alkoxy groups in (ii) the alkoxide compound capable of being reacted with the aforementioned (i) copper compound to produce a copper alkoxide with respect to the copper atoms in (i) the copper compound not containing halogen atoms (alkoxy groups/Cu) is 0.05–2.0 mol, and preferably 0.1–1.2 mol.

When catalysts 1, 2, 3, or 5 are used, one may also add a hydroacid halide (halide acid) together with the catalyst.

Next, carbon monoxide and oxygen gas are introduced under pressure into the alcohol containing catalytic components. Moreover, the carbon monoxide and oxygen may be introduced into the alcohol containing catalytic components individually, or they may be premixed and introduced together. At this stage, gases that do not generate the reaction product, specifically hydrogen, nitrogen, carbon dioxide, methane, and inert gases such as argon, may be present in the reaction system.

The amount of carbon monoxide introduced should preferably be greater than the stoichiometric number. For this reason, the molar ratio of the carbon dioxide to the oxygen introduced (carbon dioxide/oxygen) should be within the range of 3/1–100/1, and preferably 20/1–100/1.

The reaction is ordinarily carried out at a temperature of 50–200° C., and preferably 100–150° C., and a pressure of atmospheric pressure to 150 atmospheres, with a pressure of 10–100 atmospheres being preferred.

Dialkyl carbonate is produced by the above reaction.

By means of the present invention, the yield of dialkyl carbonate obtained can be increased.

Moreover, the dialkyl carbonate produced can be recovered by a separation method known in the art, such as distillation, filtering, decanting, centrifugation, demixing, or permeation membrane separation. These separation methods may also be used in combinations of two or more.

Catalysts contained in the reaction solution of recovered dialkyl carbonate and unreacted alcohol, etc., may be recovered and reused.

This type of reaction may be carried out using a batch-tank reaction vessel or a continuous reaction vessel. It is particularly preferable to use a pressure-resistant vessel such as an autoclave.

In the case of a continuous reaction vessel, the alcohol, carbon monoxide, and oxygen are introduced into the solution of the aforementioned alcohol containing catalytic components and reacted. Next, the reaction solution containing the dialkyl carbonate produced, water, and alcohol, the unreacted carbon monoxide, and water vapor are removed, the dialkyl carbonate and water are removed from the reaction solution, and the other components are recycled into the reaction system.

The reaction solution into which alcohol, carbon monoxide, oxygen, and if necessary, a hydroacid halide have been introduced may also contain unrecovered dialkyl carbonate. The reaction solution into which alcohol, carbon monoxide, oxygen, and if necessary, a hydroacid halide have been supplied should have an alcohol concentration of 30–80% by weight, and preferably 35–80% by weight, and a water concentration of 1–10% by weight, and preferably 2–7% by weight.

In the above method for manufacturing dialkyl carbonate of the present invention, the aforementioned catalysts 1–5 are used as catalysts; by using these catalysts, it becomes possible to efficiently manufacture dialkyl carbonate while maintaining high catalytic activity.

According to the method for manufacturing dialkyl carbonate of the present invention, a combination of specified catalysts is used, so that by means of these catalysts, it becomes possible to efficiently manufacture dialkyl carbonate while maintaining a high degree of catalytic activity without clogging of the tubing or reaction vessel. Moreover, when diaryl carbonate manufactured using dialkyl carbonate obtained in this manner as a raw material is used in polycondensation of polycarbonate, it is possible to obtain polycarbonate having a favorable color tone, and this type of polycarbonate is better suited than general molding materials for use in applications including construction materials such as sheets, automobile headlight lenses, optical lenses for glasses, etc., and optical recording materials, and it is particularly well-suited for molded materials used in optical disks.

WORKING EXAMPLES

The following is a concrete explanation of the present invention by means of working examples, but the invention is by no means limited to these examples.

Working Example 1

47.2 g of methanol, 6.96 g of cupric chloride, and 2.25 g of aluminum triethoxide ($Al(OC_2H_5)_3$) (Al/Cu molar ratio= 0.27) was placed in a hastelloy autoclave with an internal volume of 300 mL and sealed.

Next, the autoclave was heated to 125° C., the reaction gas (composition: $O_2$=4.87%, $N_2$=3.59%, CO=91.54%, $CO_2$=0.00%) was fed into the autoclave at the rate of 18.7 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 6.5 mol %, and the amount of dimethyl carbonate produced was 5.7 g.

Working Example 2

47.5 g of methanol, 6.96 g of cupric chloride, and 4.21 g of aluminum triethoxide ($Al(OC_2H_5)_3$) (Al/Cu molar ratio= 0.51) was placed in a hastelloy autoclave having an internal volume of 300 mL and sealed.

Next, the autoclave was heated to 125° C., the same reaction gas as that used in Working Example 1 was fed into the autoclave at the rate of 18.5 mL/min to a total pressure of 2.5–2.6 MPa, and the mixture was reacted 60 minutes.

After the autoclave was cooled, the unreacted gas was slowly purged, the reaction solution was removed, and the post-reaction gas composition and reaction mixture composition were quantitatively analyzed by gas chromatography.

Moreover, the methanol-dimethyl carbonate conversion rate was 6.6 mol %, and the amount of dimethyl carbonate produced was 4.17 g.

Working Example 3

47.1 g of methanol, 6.98 g of cupric chloride and 2.52 g of titanium trimethoxide ($Ti(OCH_3)_4$) (Ti/Cu molar ratio= 0.29) was placed in a hastelloy autoclave having an internal volume of 300 mL and sealed.

Next, the autoclave was heated to 125° C., and the same reaction gas as that used in Working Example 1 was fed into the autoclave at a rate of 18.5 mL/min to a total pressure of 2.5–2.6 MPa, and the reaction was carried out for 60 minutes.

After the autoclave was cooled, the unreacted gas was slowly removed, the reaction solution was removed, and the post-reaction gas composition and reaction solution composition were quantitatively analyzed by gas chromatography.

The methanol-dimethyl carbonate conversion rate was 6.1 mol %, and the amount of dimethyl carbonate produced was 3.87 g.

Working Example 4

48.3 g of methanol, 3.99 g of aluminum chloride ($AlCl_3$) (Al/Cu molar ratio=0.58) and 4.31 g of sodium methoxide ($NaOCH_3$) (molar ratio of (Cl in aluminum chloride/ methoxy groups in sodium methoxide)=1.12) was placed sequentially in a hastelloy autoclave having an internal volume of 300 mL, after which 6.98 g of cupric chloride was added and the autoclave was sealed.

Next, the temperature of the autoclave was increased to 125° C., the reaction gas (composition: $O_2$=5.07%, $N_2$=6.15%, CO=88.80%, $CO_2$=0.00%) was fed into the autoclave at 20.0 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 5.5 mol %, and the amount of dimethyl carbonate produced was 3.54 g.

Working Example 5

48.6 g of methanol, 5.53 g of cuprous chloride, and 1.04 mg of magnesium chloride ($MgCl_2$) (Mg/Cu molar ratio=0.195) was placed in a hastelloy autoclave having an internal volume of 300 mL, and the autoclave was sealed.

Next, the autoclave was heated to 115° C., the reaction gas (composition: $O_2$=4.31%, $N_2$=1.57%, CO=93.83%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 6.6 mol %, and the amount of dimethyl carbonate produced was 4.28 g.

Working Example 6

46.9 g of methanol, 5.54 g of cuprous chloride, and 2.05 g of magnesium chloride ($MgCl_2$) (Mg/Cu molar ratio=0.384) was placed in a hastelloy autoclave with an internal volume of 300 mL.

Next, the autoclave was heated to 115° C., and the reaction gas (composition: $O_2$=4.78%, $N_2$=0.32%, CO=94.90%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 7.6 mol %, and the amount of dimethyl carbonate produced was 4.75 g.

Working Example 7

48.4 g of methanol, 6.98 g of cupric chloride ($CUCl_2$), and 1.06 g of magnesium chloride ($MgCl_2$) (Mg/Cu molar ratio=0.214) was placed in a hastelloy autoclave having an internal volume of 300 mL, and the autoclave was sealed.

Next, the autoclave was heated to 115° C., the reaction gas (composition: $O_2$=4.31%, $N_2$=1.57%, CO=93.83%, $CO_2$=0.00%) was fed into the autoclave to a total pressure of 2.5–2.6 MPa, and the reaction was carried out for 30 minutes. After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 6.2 mol %, and the amount of dimethyl carbonate produced was 4.01 g.

Working Example 8

47.0 g of methanol, 5.11 g of cuprous chloride, and 1.97 g of calcium chloride ($CaCl_2$) (Ca/Cu molar ratio=0.344) was placed in a hastelloy autoclave having an internal volume of 300 mL, and the autoclave was sealed.

Next, the autoclave was heated to 115° C., the reaction gas (composition: $O_2$=4.31%, $N_2$=1.57%, CO=93.83%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 7.8 mol %, and the amount of dimethyl carbonate produced was 4.88 g.

Working Example 9

47.2 g of methanol, 5.07 g of cuprous chloride, and 4.14 g of barium chloride ($BaCl_2 \cdot 2H_2O$) (Ba/Cu molar ratio=0.336) was placed in a hastelloy autoclave having an internal volume of 300 mL, and the autoclave was sealed.

Next, the autoclave was heated to 115° C., the reaction gas (composition: $O_2$=4.31%, $N_2$=1.57%, CO=93.83%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 7.1 mol %, and the amount of dimethyl carbonate produced was 4.49 g.

Working Example 10

47.3 g of methanol, 6.35 g of copper dimethoxide (Cu($OCH_3$)$_2$), and 2.97 g of 36% hydrochloric acid (Cl/Cu molar ratio 0.58) was placed in a hastelloy autoclave with an internal volume of 300 mL, and the autoclave was sealed.

Next, the autoclave was heated to 125° C., the reaction gas (composition: $O_2$=5.93%, $N_2$=1.05%, CO=93.02%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 5.4 mol %, and the amount of dimethyl carbonate produced was 3.44 g.

Working Example 11

46.7 g of methanol, 6.20 g of copper dimethoxide (Cu($OCH_3$)$_2$), and 4.21 g of 36% hydrochloric acid (Cl/Cu molar ratio=0.84) was placed in a hastelloy autoclave with an internal volume of 300 mL, and the autoclave was sealed.

Next, the autoclave was heated to 125° C., the reaction gas (composition: $O_2$=4.63%, $N_2$=4.67%, CO=90.70%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 10.4 mol %, and the amount of dimethyl carbonate produced was 6.63 g.

Working Example 12

47.6 g of methanol, 5.04 g of cupric hydroxide ($Cu(OH)_2$), and 2.97 g of 36% hydrochloric acid (Cl/Cu molar ratio=0.55) was placed in a hastelloy autoclave having an internal volume of 300 mL, and the autoclave was sealed.

Next, the autoclave was heated to 125° C., the reaction gas (composition: $O_2$=4.54%, $N_2$=4.38%, CO=91.08%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 5.5 mol %, and the amount of dimethyl carbonate produced was 3.51 g.

Working Example 13

48.8 g of methanol, 9.29 g of cupric acetate ($Cu(OCOCH_3)_2$), and 5.11 g of 36% hydrochloric acid (Cl/Cu molar ratio=0.99) was placed in a hastelloy autoclave with an internal volume of 300 mL, and the autoclave was sealed.

Next, the autoclave was heated to 125° C., the reaction gas (composition: $O_2$=5.08%, $N_2$=2.53%, CO=92.39%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 3.3 mol %, and the amount of dimethyl carbonate produced was 2.15 g.

Working Example 14

47.3 g of methanol, 6.13 g of basic copper carbonate ($CuCO_3 \cdot Cu(OH) \cdot H_2O$), and 5.00 g of 36% hydrochloric acid (Cl/Cu molar ratio=0.96) was placed in a hastelloy autoclave with an internal volume of 300 mL, and the autoclave was sealed.

Next, the autoclave was heated to 125° C., the reaction gas (composition: $O_2$=6.18%, $N_2$=0.83%, CO=92.99%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 9.0 mol %, and the amount of dimethyl carbonate produced was 5.70 g.

Working Example 15

47.4 g of methanol, 9.27 g of cupric acetate, and 1.92 g of sodium methoxide ($NaOCH_3/Cu(OCOCH_3)_2$ molar ratio=0.7) was placed in a hastelloy autoclave with an internal volume of 300 mL, and the autoclave was sealed.

Next, the autoclave was heated to 125° C., the reaction gas (composition: $O_2$=4.16%, $N_2$=1.52%, CO=94.32%, $CO_2$=0.00%) were fed into the autoclave at a rate of 27.0 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 2.9 mol %, and the amount of dimethyl carbonate produced was 1.84 g.

Working Example 16

47.0 g of methanol, 5.06 g of cupric hydroxide ($Cu(OH)_2$), and 1.36 g of sodium methoxide ($NaOCH_3/Cu(OH)_2$ molar ratio=0.48) was placed in a hastelloy autoclave with an internal volume of 300 mL, and the autoclave was sealed.

Next, the autoclave was heated to 125° C., the reaction gas (composition: $O_2$=4.54%, $N_2$=4.38%, CO=91.08%, $CO_2$=0.00%) was fed into the autoclave at a rate of 17.5 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 3.4 mol %, and the amount of dimethyl carbonate produced was 2.16 g.

Working Example 17

48.7 g of methanol, 4.97 g of cupric sulfate (CuS), and 2.07 g of sodium methoxide ($NaOCH_3$/CuS molar ratio 0.74) was placed in a hastelloy autoclave with an internal volume of 300 mL, and the autoclave was sealed.

Next, the autoclave was heated to 125° C., the reaction gas (composition: $O_2$=5.08%, $N_2$=2.53%, CO=92.39%, $CO_2$=0.00%) was fed into the autoclave at a rate of 17.5 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 3.7 mol %, and the amount of dimethyl carbonate produced was 2.38 g.

Working Example 18

47.7 g of methanol, 9.20 g of cupric acetate, and 2.56 g of potassium methoxide ($KOCH_3/Cu(OCOCH_3)_2$ molar ratio=0.72) was placed in a hastelloy autoclave with an internal volume of 300 mL, and the autoclave was sealed.

Next, the autoclave was heated to 125°vC., and the reaction gas (composition: $O_2$=4.16%, $N_2$=1.52%, CO=94.32%, $CO_2$=0.00%) was fed into the autoclave at a rate of 24.1 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 2.5 mol %, and the amount of dimethyl carbonate produced was 1.61 g.

Moreover, in Working Examples 1–18, the production of methylal as a byproduct was confirmed in all cases.

Comparison Example 1

46.5 g of methanol and 6.92 g of cupric chloride was placed in a hastelloy autoclave with an internal volume of 300 mL, and the autoclave was sealed.

Next, the autoclave was heated to 125° C., the reaction gas (composition: $O_2$=5.07%, $N_2$=6.15%, CO=88.88%, $CO_2$=0.00%) was fed into the autoclave at a rate of 31.0 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 5.0 mol %, and the amount of dimethyl carbonate produced was 3.14 g.

Comparison Example 2

47.2 g of methanol and 5.43 g of cuprous chloride was placed in a hastelloy autoclave with an internal volume of 300 mL, and the autoclave was sealed.

Next, the autoclave was heated to 115° C., the reaction gas (composition: $O_2$=4.40%, $N_2$=0.54%, CO=95.03%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 5.6 mol %, and the amount of dimethyl carbonate produced was 3.55 g.

Comparison Example 3

47.1 g of methanol and 7.04 g of cupric chloride ($CuCl_2$) was placed in a hastelloy autoclave with an internal volume of 300 mL, and the autoclave was sealed.

Next, the autoclave was heated to 115° C., the reaction gas (composition: $O_2$=4.40%, $N_2$=0.54%, CO=95.03%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

Moreover, the methanol-dimethyl carbonate conversion rate was 5.4 mol %, and the amount of dimethyl carbonate produced was 3.37 g.

Comparison Example 4

46.7 g of methanol and 6.20 g of copper dimethoxide ($Cu(OCH_3)_2$) was placed in a hastelloy autoclave with an internal volume of 300 mL, and the autoclave was sealed.

Next, the autoclave was heated to 125° C., the reaction gas (composition: $O_2$=5.93%, $N_2$=1.05%, CO=93.02%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 0.8 mol %, and the amount of dimethyl carbonate produced was 0.53 g.

The production of methylal as a byproduct was confirmed.

Comparison Example 5

47.7 g of methanol and 5.04 g of cupric hydroxide ($Cu(OH)_2$) was placed in a hastelloy autoclave with an internal volume of 300 mL, and the autoclave was sealed.

Next, the autoclave was heated to 125° C., the reaction gas (composition: $O_2$=5.08%, $N_2$=8.44%, CO=85.88%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 0.2 mol %, and the amount of dimethyl carbonate produced was 0.14 g.

The production of methylal as a byproduct was confirmed.

Comparison Example 6

47.2 g of methanol and 9.23 g of cupric acetate ($Cu(OCOCH_3)_2$) was placed in a hastelloy autoclave with an internal volume of 300 mL, and the autoclave was sealed.

Next, the autoclave was heated to 125° C., and the reaction gas (composition: $O_2$=5.08%, $N_2$=2.53%, CO=92.39%, $CO_2$=0.00%) was fed into the autoclave at a rate of 25.0 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 0.7 mol %, and the amount of dimethyl carbonate produced was 0.47 g.

The production of methylal as a byproduct was confirmed.

Comparison Example 7

47.7 g of methanol and 6.10 g of basic copper carbonate ($CuCO_3 \cdot Cu(OH)_2 \cdot H_2O$) was placed in a hastelloy autoclave with an internal volume of 300 mL, and the autoclave was sealed.

Next, the autoclave was heated to 125° C., the reaction gas (composition: $O_2$=6.50%, $N_2$=0.60%, CO=92.90%, $CO_2$=0.00%) was fed into the autoclave to a total pressure of 2.5–2.6 MPa, and the reaction was carried out for 30 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 0.1 mol %, and the amount of dimethyl carbonate produced was 0.08 g.

The production of methylal as a byproduct was confirmed.

Comparison Example 8

47.2 g of methanol and 5.11 g of cupric hydrochloride ($Cu(OH)_2$) was placed in a hastelloy autoclave with an internal volume of 300 mL, and the autoclave was sealed.

Next, the autoclave was heated to 125° C., the reaction gas (composition: $O_2$=5.08%, $N_2$=8.44%, CO=85.88%, $CO_2$=0.00%) was fed into the autoclave at a rate of 27.0 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 0.3 mol %, and the amount of dimethyl carbonate produced was 0.23 g.

The production of methylal as a byproduct was confirmed.

Comparison Example 9

47.9 g of methanol and 4.91 g of cupric sulfate (CuS) was placed in a hastelloy autoclave with an internal volume of 300 mL, and the autoclave was sealed.

Next, the autoclave was heated to 125° C., the reaction gas (composition: $O_2$=5.08%, $N_2$=8.44%, CO=85.88%, $CO_2$=0.00%) was supplied to the autoclave at a rate of 21.5 mL/min to a total pressure of 2.5–2.6 MPa, and the reaction was carried out for 60 minutes.

After the autoclave was cooled, the unreacted gas was slowly purged, the reaction solution was removed, and the post-reaction gas composition and reaction solution composition were quantitatively analyzed by gas chromatography.

The resulting methanol-dimethyl carbonate conversion rate was 0.2 mol %, and the amount of dimethyl carbonate produced was 0.11 g.

The production of methylal as a byproduct was confirmed.

What is claimed is:

1. Method for manufacturing dialkyl carbonate, which method comprises reacting together carbon monoxide, oxygen and alcohol in the presence of a catalyst, which catalyst is produced by combining together ingredients comprising a cupric halide and an alkoxide compound of a metal selected from groups III through VIII of the periodic table.

2. The method for manufacturing dialkyl carbonate according to claim 1, wherein the catalyst further comprises a compound selected from the group consisting of an alkali metal alkoxide, an alkaline earth metal alkoxide, a quaternary ammonium alkoxide having formula (1), $$R^1R^2R^3R^4NOR^5 \quad (1)$$

and a quarternary phosphonium alkoxide having formula (2), $$R^1R^2R^3R^4POR^5 \quad (2)$$

where $R^1$–$R^4$ may be the same or different and denote hydrogen atoms or hydrocarbon groups having 1–20 carbon atoms, and $R^5$ denotes a hydrocarbon group having 1–20 carbon atoms).

3. The method for manufacturing dialkyl carbonate according to claim 1, wherein the aforementioned alkoxide compound of a metal from groups III through VIII of the periodic table is used in an amount of 0.05–2.0 mol with respect to the cupric halide.

4. The method for manufacturing dialkyl carbonate according to claim 2, wherein the aforementioned halide of a metal from groups III through VIII of the periodic table is used in the amount of 0.05–2.0 mol with respect to the cupric halide.

5. The method for manufacturing dialkyl carbonate, which method comprises reacting together carbon monoxide, oxygen, and alcohol in the presence of a catalyst, which catalyst produced by combining together ingredients comprising (I) a copper halide, and (II) an alkaline earth metal halide.

6. The method for manufacturing dialkyl carbonate according to claim 5, wherein the copper halide compound is cuprous chloride.

7. The method for manufacturing dialkyl carbonate according to claim 5, wherein the alkaline earth metal halide is magnesium chloride or barium chloride.

8. The method for manufacturing dialkyl carbonate, which method comprises reacting together carbon monoxide, oxygen, and alcohol in the presence of a catalyst, which catalyst comprises (a) a copper compound not containing halogen atoms, and (b) an acid halide.

9. The method for manufacturing dialkyl carbonate according to claim 8, wherein the copper compound not containing halogen atoms is at least one copper compound selected from the group consisting of copper dimethoxide, copper diethoxide, copper dipropoxide, cupric hydroxide ($Cu(OH)_2$), cupric nitrate ($Cu(NO_3)_2$), cupric acetate ($Cu(OCOCH_3)_2$), cupric sulfate ($CuSO_4$), and basic copper carbonate ($CuCO3 \cdot Cu(OH) \cdot H_2O$).

10. The method for manufacturing dialkyl carbonate according to claim 8, wherein the halide acid is hydrochloric acid.

11. The method for manufacturing dialkyl carbonate, which method comprises reacting carbon monoxide, oxygen, and alcohol in the presence of a catalyst, which catalyst is produced by combining together ingredients comprising:

(A) a copper compound not containing halogen atoms, and (B) an alkoxide compound that can react with the aforementioned (A) copper compound to produce a copper alkoxide.

12. The method for manufacturing dialkyl carbonate according to claim 11, wherein the copper compound not containing halogen atoms is at least one copper compound selected from the group composed of cupric hydroxide ($Cu(OH)_2$), cupric nitrate ($Cu(NO_3)_2$), cupric acetate ($Cu(OCOCH_3)_2$), cupric sulfate ($CuSO_4$), basic copper carbonate ($CuCO_3 \cdot Cu(OH) \cdot H_2O$), and cupric sulfate (CuS).

13. The method for manufacturing dialkyl carbonate according to claim 11, wherein the alkoxide compound capable of producing a copper alkoxide is at least one compound selected from the group composed of an alkali metal alkoxide, an alkaline earth metal alkoxide, a quaternary ammonium alkoxide having formula (7) below, $$R^1R^2R^3R^4NOR^5 \quad (7)$$

and a quaternary phosphonium alkoxide having formula (8) below;

$R^1R^2R^3R^4POR^5$ (8)

(wherein $R^1$–$R^4$ may be the same or different and denote hydrogen atoms or hydrocarbon groups having 1–20 carbon atoms, and $R^5$ denotes a hydrocarbon group having 1–20 carbon atoms.

14. The method for manufacturing dialkyl carbonate according to claim 11, wherein the alkoxide compound capable of producing a copper alkoxide is used in an amount of 0.05–2.0 mol with respect to the copper compound not containing halogen atoms.

15. The method for manufacturing dialkyl carbonate according to claim 1, 5, 8 or 11 wherein the alcohol is methanol.

16. A method of making aromatic polycarbonate, which method comprises reacting a dialkyl carbonate with a dihydroxy compound where the dialkyl carbonate is made according to the method of claim 1, 5, 8, or 11.

* * * * *